(12) United States Patent
Tüysüz et al.

(10) Patent No.: US 12,357,808 B1
(45) Date of Patent: Jul. 15, 2025

(54) CONNECTOR ASSEMBLY FOR COMMUNICATION OF MEDICAL LIQUIDS

(71) Applicant: Asset Medical, Inc., San Diego, CA (US)

(72) Inventors: Mehmet Tüysüz, Mugla (AR); Ahmet Reha Basaran, Balikesir (AR)

(73) Assignee: Asset Medical, Inc., San Diego, CA (US)

( * ) Notice: Subject to any disclaimer, the term of this patent is extended or adjusted under 35 U.S.C. 154(b) by 0 days.

(21) Appl. No.: 18/397,264

(22) Filed: Dec. 27, 2023

(51) Int. Cl.
*A61M 39/10* (2006.01)

(52) U.S. Cl.
CPC . *A61M 39/1011* (2013.01); *A61M 2039/1033* (2013.01); *A61M 2039/1088* (2013.01)

(58) Field of Classification Search
CPC .............. A61M 39/1011; A61M 39/26; A61M 2039/1033; A61M 2039/1088
See application file for complete search history.

(56) References Cited

U.S. PATENT DOCUMENTS

| | | | | |
|---|---|---|---|---|
| 5,820,601 A * | 10/1998 | Mayer | ............ | A61M 39/26 604/533 |
| 6,029,946 A * | 2/2000 | Doyle | ............ | A61M 39/26 604/249 |
| 6,183,448 B1 * | 2/2001 | Mayer | ............ | A61M 39/26 604/167.02 |
| 9,089,682 B2 * | 7/2015 | Yeh | ............ | A61M 39/10 |
| 9,370,651 B2 * | 6/2016 | Zollinger | ............ | A61M 39/22 |
| 9,695,953 B2 * | 7/2017 | Burnard | ............ | F16K 15/147 |
| 9,925,365 B1 * | 3/2018 | Ryan | ............ | A61M 39/26 |
| 10,478,607 B2 * | 11/2019 | Truitt | ............ | A61M 39/105 |
| 11,123,534 B2 * | 9/2021 | Chen | ............ | A61M 39/10 |
| 11,690,993 B1 * | 7/2023 | Dikeman | ............ | A61M 39/22 604/154 |
| 11,904,131 B2 * | 2/2024 | Feith | ............ | A61M 39/14 |
| 11,931,540 B1 * | 3/2024 | Tüysüz et al. | ............ | A61M 39/20 |
| 2003/0141477 A1 * | 7/2003 | Miller | ............ | F16K 15/1825 251/149.1 |
| 2007/0218757 A1 * | 9/2007 | Guala | ............ | A61M 39/10 439/589 |
| 2009/0057589 A1 * | 3/2009 | Thorne, Jr. | ............ | A61M 39/26 251/149.1 |

(Continued)

FOREIGN PATENT DOCUMENTS

TR 200906911 A1 * 9/2009 .......... A61M 39/045

*Primary Examiner* — Nathan R Price
*Assistant Examiner* — Adam J. Cermak
(74) *Attorney, Agent, or Firm* — Carter, DeLuca & Farrell LLP; George Likourezos

(57) ABSTRACT

A connector assembly for communication of medical liquids includes an attachment part for removably engaging a delivery device, a connection part for connecting a container, and a flexible sealing member circumferentially enclosed between the attachment part and connection part around a main axis. The sealing member includes a cylindrical body extending along the axis and a sealing head at an axially distal end of the sealing member with regard to the body. The attachment part includes a first inner wall surface that extends transverse or orthogonal with respect to the axis, and opposes the connection part in the direction of axis. The body is shaped and sized for maintaining a non-contact mechanical status with regard to the first inner wall surface.

20 Claims, 11 Drawing Sheets

(56) References Cited

U.S. PATENT DOCUMENTS

| | | | | |
|---|---|---|---|---|
| 2010/0004618 A1* | 1/2010 | Rondeau | ............... | A61M 39/26 604/407 |
| 2011/0319838 A1* | 12/2011 | Goral | ........................ | B26F 1/14 604/533 |
| 2011/0319859 A1* | 12/2011 | Zeytoonian | ......... | A61M 39/045 604/246 |
| 2012/0089086 A1* | 4/2012 | Hokanson | ............ | A61M 39/045 604/68 |
| 2014/0276463 A1* | 9/2014 | Mansour | ............... | A61M 39/22 604/256 |
| 2015/0008664 A1* | 1/2015 | Tachizaki | ............ | A61M 39/045 285/45 |
| 2015/0141937 A1* | 5/2015 | Bonaldo | ............ | A61M 39/1011 604/256 |
| 2016/0228687 A1* | 8/2016 | Chih | ..................... | A61M 39/26 |
| 2017/0009920 A1* | 1/2017 | Canatella | ........... | A61M 39/1011 |
| 2017/0080203 A1* | 3/2017 | Yeh | ..................... | A61M 39/045 |
| 2018/0015278 A1* | 1/2018 | Ueda | ..................... | A61M 39/26 |
| 2018/0185627 A1* | 7/2018 | Chelak | ................. | A61B 5/0215 |
| 2018/0296820 A1* | 10/2018 | Bogoslofski | ........ | F16K 11/0833 |
| 2019/0001112 A1* | 1/2019 | Takeuchi | ............. | A61M 39/26 |
| 2019/0070400 A1* | 3/2019 | Chelak | ................. | B29C 64/106 |
| 2019/0117953 A1* | 4/2019 | Ueda | ................. | A61M 39/1011 |
| 2020/0222681 A1* | 7/2020 | Burkholz | .............. | A61M 39/26 |
| 2020/0254195 A1* | 8/2020 | Nakagami | ............ | A61M 5/165 |
| 2020/0376254 A1* | 12/2020 | Isaacson | ........... | A61M 25/0693 |
| 2021/0220633 A1* | 7/2021 | Feith | ..................... | A61M 39/10 |
| 2021/0393938 A1* | 12/2021 | Lynn | ..................... | A61M 39/10 |
| 2022/0032031 A1* | 2/2022 | Feith | ..................... | A61M 39/24 |
| 2022/0096816 A1* | 3/2022 | Oda | ..................... | F16L 37/413 |
| 2022/0355095 A1* | 11/2022 | Wine | ..................... | A61M 39/24 |
| 2023/0048460 A1* | 2/2023 | Tachizaki | ........... | A61M 39/1011 |
| 2023/0139756 A1* | 5/2023 | Wine | ..................... | F16L 37/30 251/149.1 |
| 2024/0075273 A1* | 3/2024 | Wine | ..................... | A61M 39/26 |
| 2024/0075274 A1* | 3/2024 | Bhaskar | ............... | A61M 39/26 |
| 2024/0342458 A1* | 10/2024 | Albertsen | ............... | A61L 29/02 |

* cited by examiner

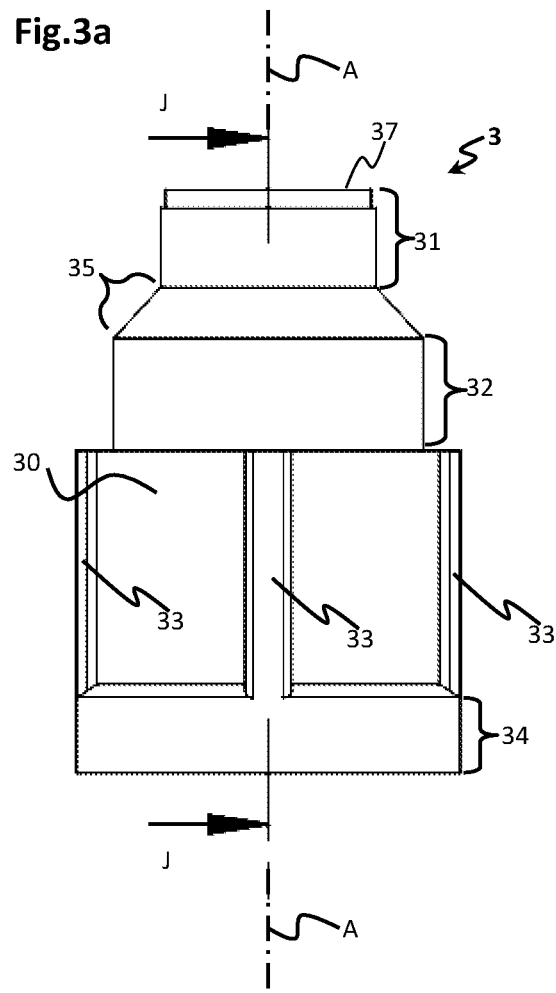
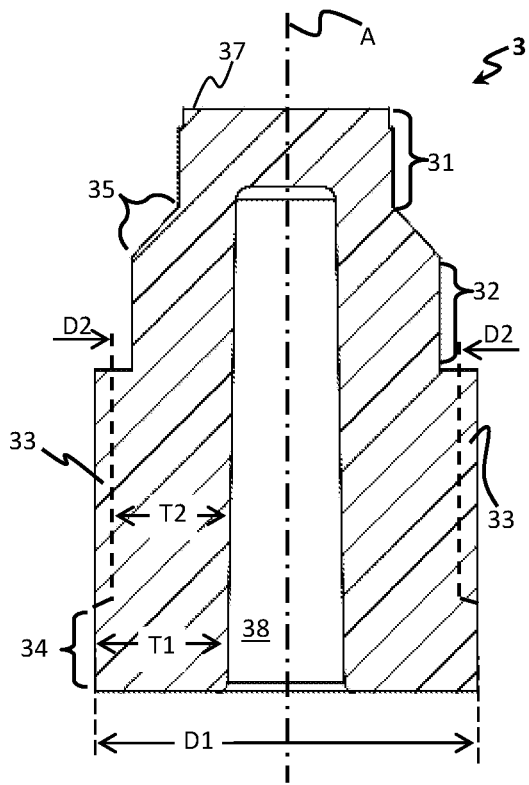
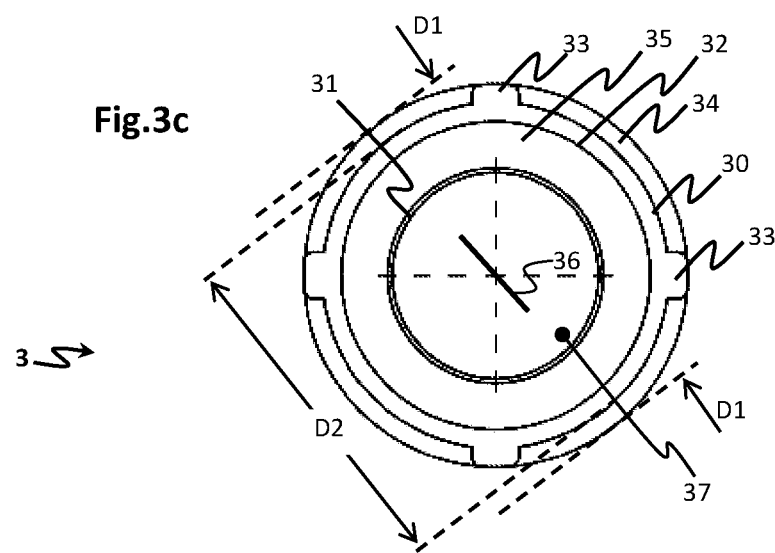

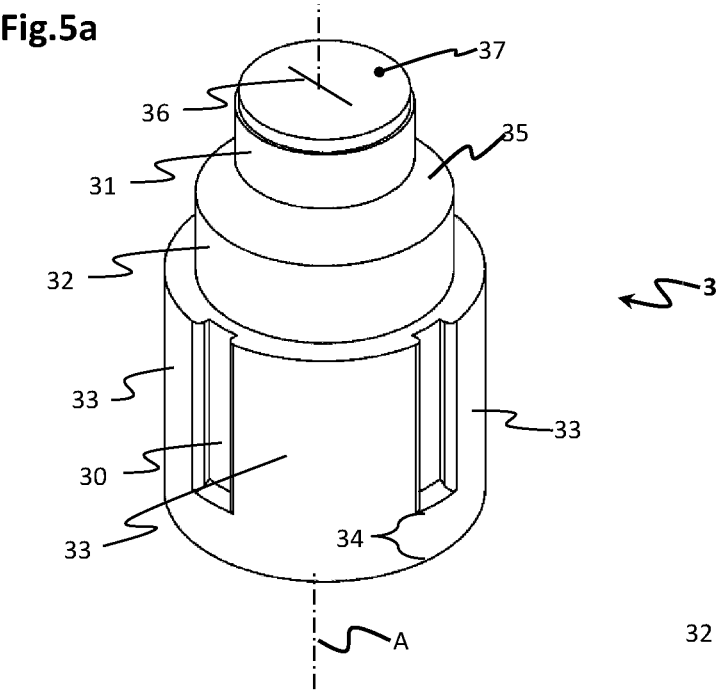
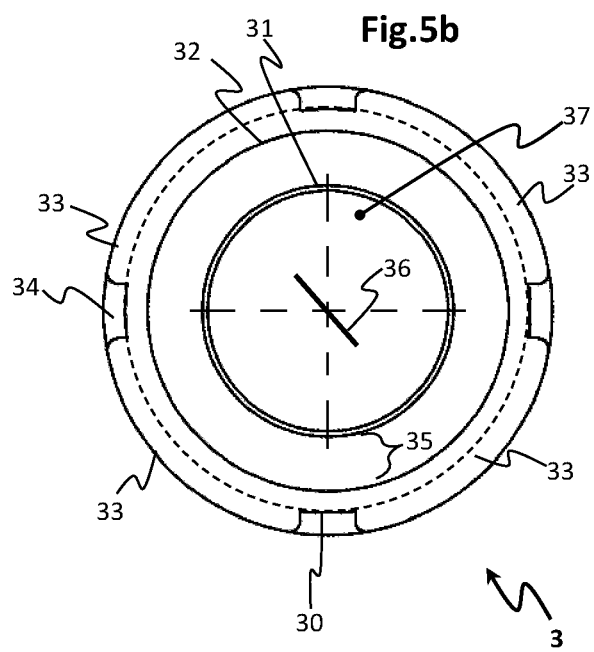
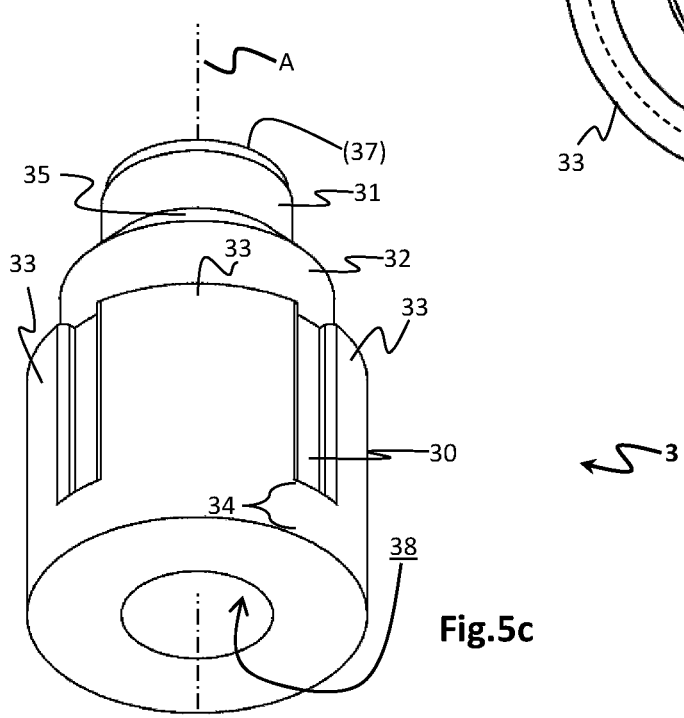

Fig.7a
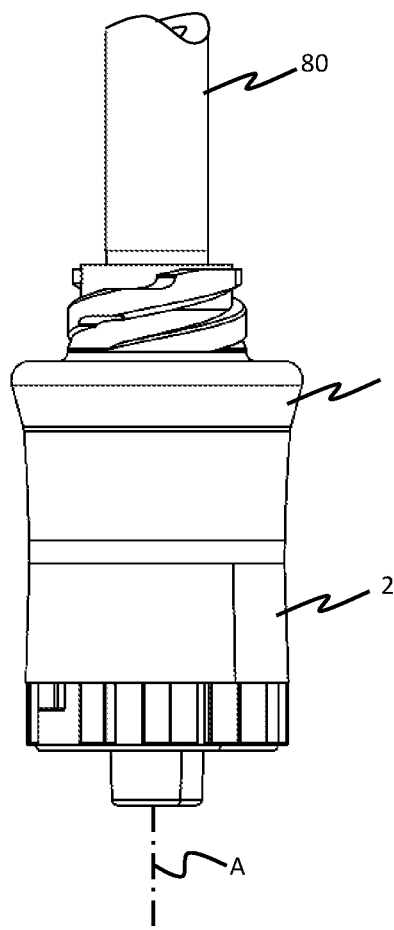
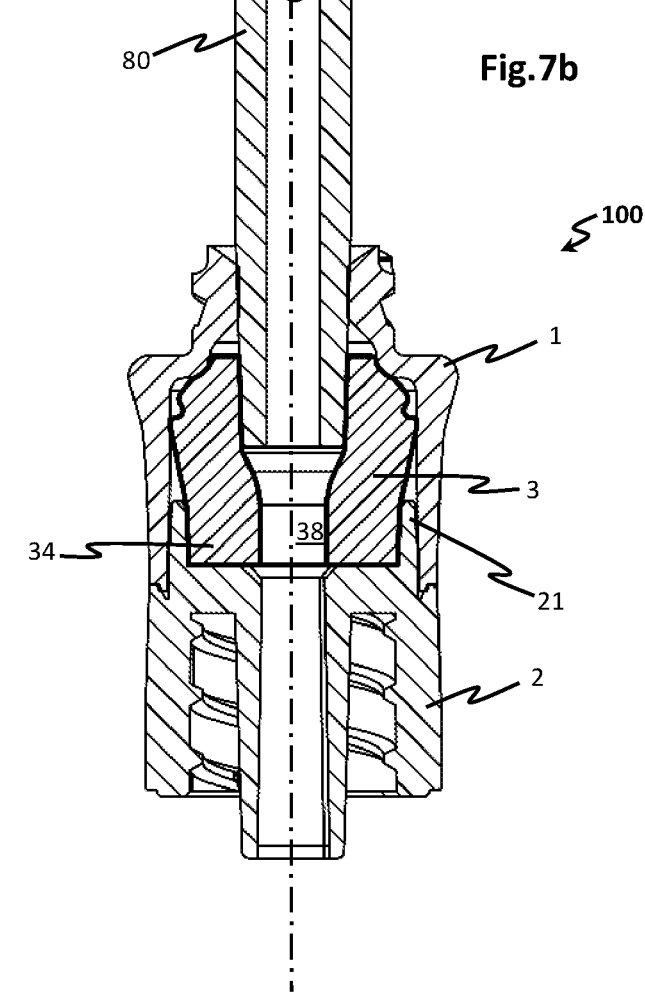
Fig.7b

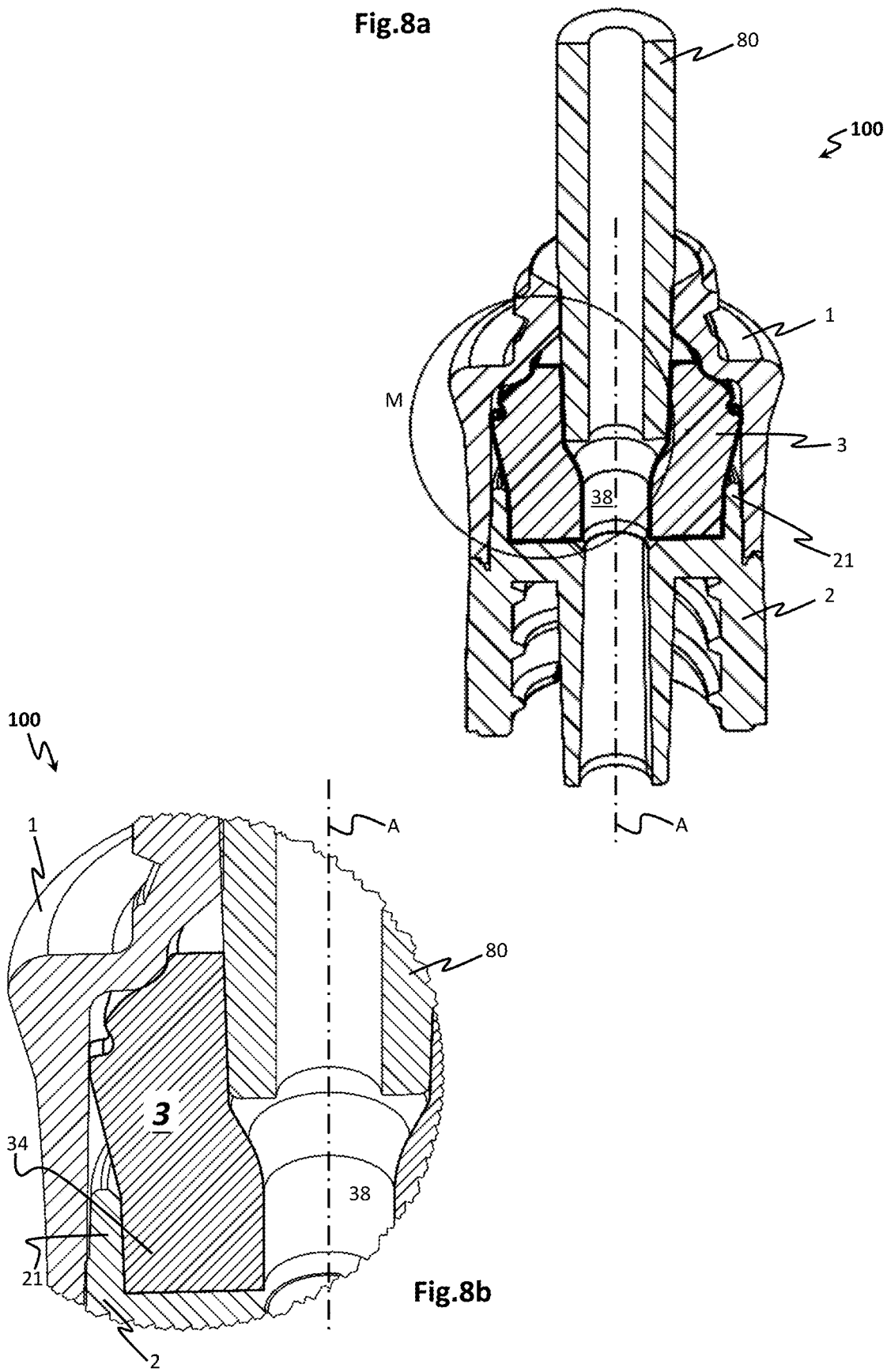

Fig.10a
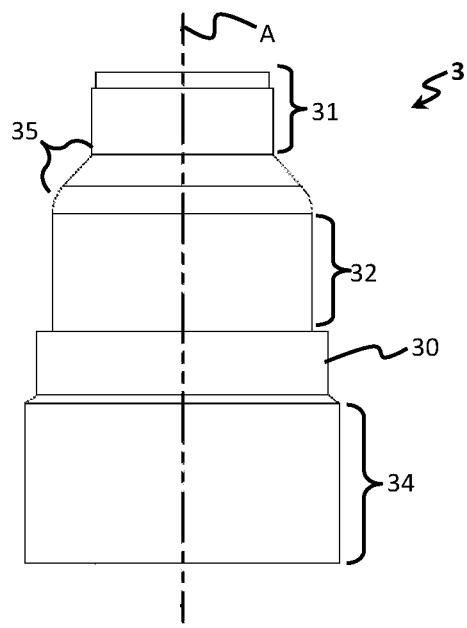
Fig.10b
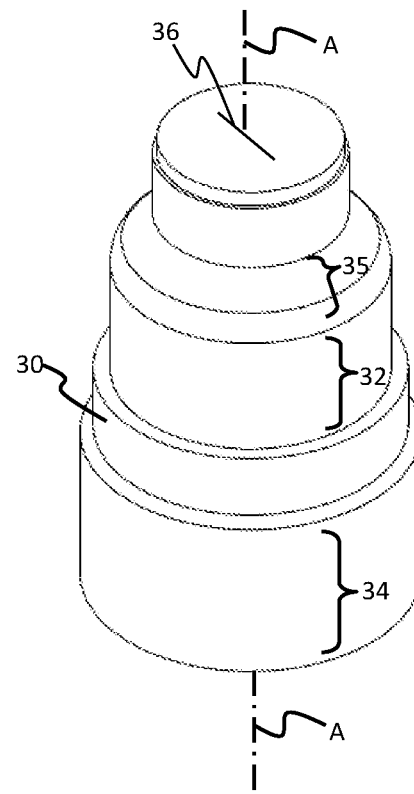
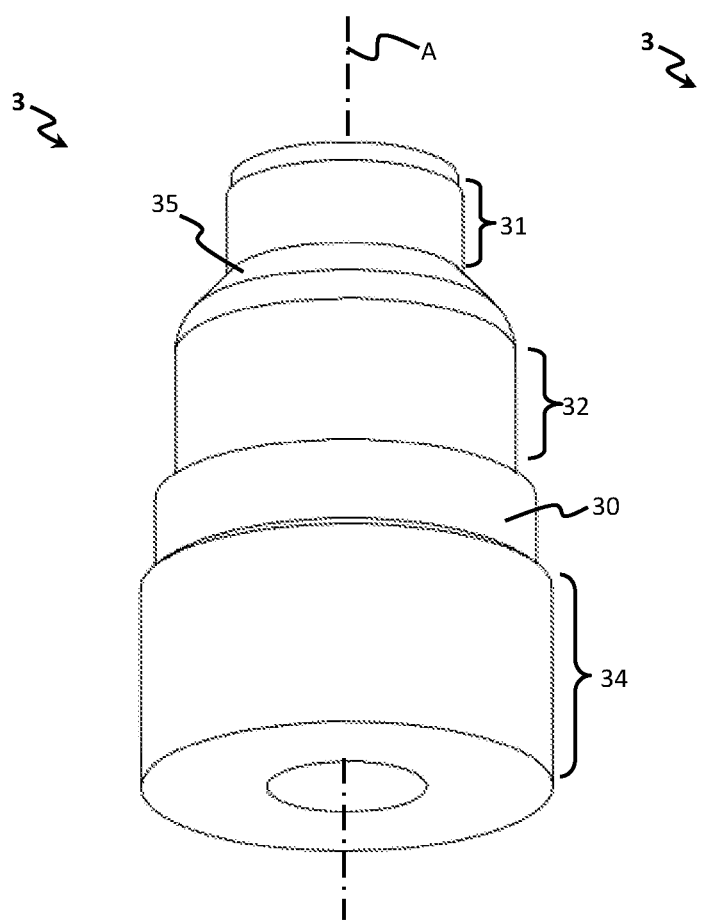
Fig.10c

CONNECTOR ASSEMBLY FOR COMMUNICATION OF MEDICAL LIQUIDS

TECHNICAL FIELD

The present application relates to a connector assembly for communication of medical liquids. In particular, the present application relates to such an assembly.

BACKGROUND

Connectors for medical liquids such as swabbable needle-free connector assemblies are used for communicating medical liquids between a delivery device and a container of a further medium in hydraulic communication with the assembly. Examples to the container of further medium include a vial, bottle, ampule, flexible bag or intravenous catheter.

TR 2009/06911 discloses a swabbable needle-free connector assembly that includes an attachment part for being removably engaged with a delivery device, a connection part for being connected to a container of a further medium, and a flexible sealing member enclosed between the attachment part and connection part. The sealing member has a sealing head with a slot opening that is accessible through an access opening on the attachment part. In a normal, closed first state, the sealing head extends into the access opening which circumferentially supports the sealing head around a main axis of the assembly. In the first state, the slot opening is closed, thereby hermetically sealing a further medium-side thereof from a delivery device-side.

When a delivery device is introduced through the access opening and forced onto the sealing head along the main axis, axial compression of the sealing member results in radial expansion thereof, and the slot opening receives a tip of the delivery device. Thus, an open second state takes place, in which the sealing is ceased and fluid communication to or from the further medium-side is established.

A flattened upper surface is not sufficient to ensure that the collapsed sealing member will return to its closed position with. If the sealing member remains lodged inside even upon cessation of axial compression, the fluid path does not close, the medical fluid such as a bodily fluid leaks out of the access opening as a connection port, creating health risk to the operator and patient. Failure of the sealing member in returning to its closed position prevents the valve surface from being swabbable, causing an IV therapy to be open to bacterial growth.

SUMMARY

In various embodiments, the present disclosure relates to a needle-free connector assembly that overcomes shortcomings in the prior art. In various embodiments, the present disclosure relates to a needle-free connector assembly that provides a facilitated use, without compromising the sealing in a closed state thereof. The objects of the disclosure are achieved by the set of features that constitute the appended claims.

In an aspect of the present disclosure, a connector assembly for communication of medical liquids includes an attachment part for removably engaging a delivery device, a connection part for connecting a container, and a flexible sealing member circumferentially enclosed between the attachment part and connection part around a main axis (A). The sealing member includes a cylindrical body extending along the axis (A), a sealing head at an axially distal end of the sealing member with regard to the body. The sealing member is arranged to have a closed first state in which the head is received into an access opening of the attachment part, and an open second state in which the head is retracted away from the access opening when compressed through the access opening along the axis (A). The attachment part includes a first inner wall surface that extends transverse or orthogonal with respect to the axis (A), and opposes the connection part in the direction of axis (A), wherein the body is shaped and sized for maintaining a non-contact mechanical status with regard to the first inner wall surface.

In an aspect of the connector assembly, the attachment part includes a second inner wall surface that opposes the sealing member radially with respect to the axis (A), such that a circumferential gap remains in-between the sealing member and the second inner wall surface at least when in the first position; and the body is sized and shaped for maintaining a positive value of distance to a second inner wall surface of the attachment part, when in the normally closed first state.

In an aspect of the connector assembly, the sealing member further includes one or more columns on a side surface of the body; the columns radially protruding away from the axis (A), and extending parallel to the axis (A) along the body; and the columns are sized and shaped for, when in the first state, maintaining a positive value of distance to respective one or more first inner wall surfaces of the attachment part.

In an aspect of the connector assembly, the columns are sized and shaped for, when in the first state, maintaining a positive value of distance to a second inner wall surface of the attachment part.

In an aspect of the connector assembly, the one or more columns of the collapsible sealing member have a tapered geometry, such that a radial width of the one or more columns decreases from the foot portion towards the cylindrical portion.

In an aspect of the connector assembly, the sealing member includes a foot portion at an axially distal end of the sealing member with regard to the head, arranged for being in mechanical communication with the connection part.

In an aspect of the connector assembly, in radial directions with regard to the axis (A), the foot portion has a greater thickness (T1) when compared to a thickness (T2) of the body.

In an aspect of the connector assembly, an inner diameter of the sealing member at the body and foot portion has an identical value or has a difference of up to 10 percent; and the foot portion has an outer diameter (D1) that is greater than an outer diameter (D2) of the body at a ratio that is greater than 10 percent.

In an aspect of the connector assembly, the outer diameter (D1) of the foot portion is greater than an outer diameter (D2) of the body at a ratio that is greater than 20 percent.

In an aspect of the connector assembly, the foot portion axially extends from the body and has a diameter (D1) that is greater than a diameter (D2) of the body.

In an aspect of the connector assembly, a half of the difference between the diameter (D1) of the foot portion and the diameter (D2) of the body is equal to a radial protrusion extent of the one or more columns.

In an aspect of the connector assembly, the attachment part includes a side wall that is sized and shaped for supporting the foot portion in radial directions towards the axis (A).

In an aspect of the connector assembly, the side wall is sized and shaped to circumferentially cover the foot portion around the axis (A).

In an aspect of the connector assembly, the sealing member includes a cylindrical portion between the body and head.

In an aspect of the connector assembly, the sealing member includes an intermediate portion between the body and head, the intermediate portion having a frusto-conical geometry, diameter of which decreases towards the head.

In an aspect of the connector assembly, the sealing member includes a cylindrical portion between the body and head, and the intermediate portion is disposed between the cylindrical portion and head.

In an aspect of the connector assembly, the sealing member includes a slot opening for receiving a tip of a delivery device when in the second state.

In an aspect of the connector assembly, the attachment part includes a female Luer lock fitting on which the access opening is formed, and the connection part includes a male Luer lock fitting in hydraulic communication with an inner cavity of the sealing member.

BRIEF DESCRIPTION OF THE DRAWINGS

FIG. 1b is H-H section of the assembly based on FIG. 1a.
FIG. 2b is another perspective view of the sealing member shown in FIG. 2a.
FIG. 3a is side view of an exemplary embodiment of the sealing member according to the present disclosure.
FIG. 3b is J-J section view of the sealing member based on FIG. 3a.
FIG. 3c is plan view of the sealing member shown in FIG. 3a.
FIG. 4b is K-K section view of the sealing member based on FIG. 4a.
FIG. 4c is plan view of the sealing member shown in FIG. 4a.
FIG. 5a shows perspective view of another exemplary embodiment of the sealing member according to the present disclosure.
FIG. 5b is plan view of the sealing member shown in FIG. 5a.
FIG. 5c is another perspective view of the sealing member shown in FIG. 5a.
FIG. 6b is exploded section view of the assembly shown in FIG. 6a.
FIG. 7a is side view of the exemplary assembly shown in FIG. 1, in engagement with a delivery device.
FIG. 7b is side section view based on FIG. 7a.
FIG. 8a is perspective section view based on FIG. 7b.
FIG. 8b is close-up view of detail M from FIG. 8a.
FIG. 9b is a perspective view of the sealing member shown in FIG. 9a.
FIG. 9c is another perspective view of the sealing member shown in FIG. 9a.
FIG. 10a is side view of an exemplary sealing member embodiment for an assembly according to the present disclosure.
FIG. 10b is a perspective view of the sealing member shown in FIG. 10a.
FIG. 10c is another perspective view of the sealing member shown in FIG. 10a.

DETAILED DESCRIPTION

With reference to the appended drawings, the present application proposes a connector assembly (100) for communication of a medical fluid. The medical fluid can be a bodily fluid such as blood, or any liquid that can be administered to a mammal; yet medically used gases, for example, air can also be considered as medical fluid within the context of the present application.

Figure 1A:
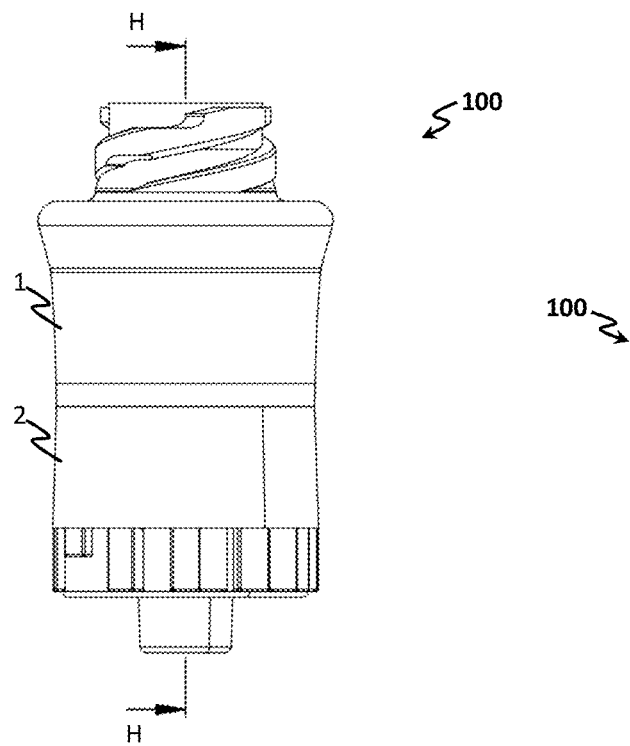
FIG. 1a is side view of an exemplary assembly according to the present disclosure.
Figure 1B:
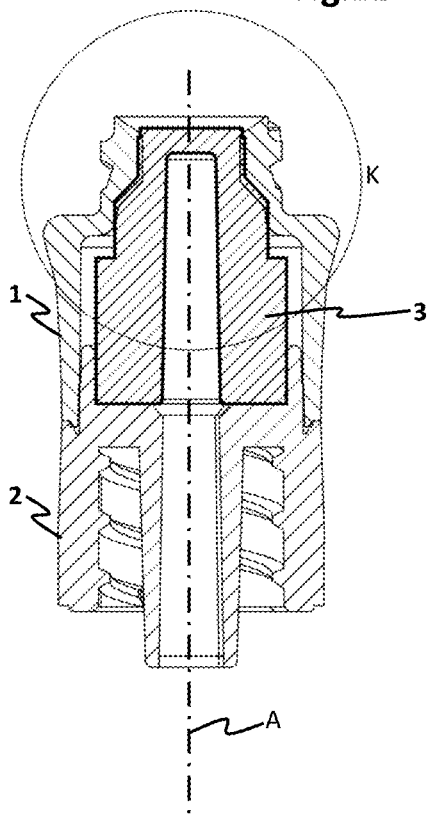
Figure 1C:
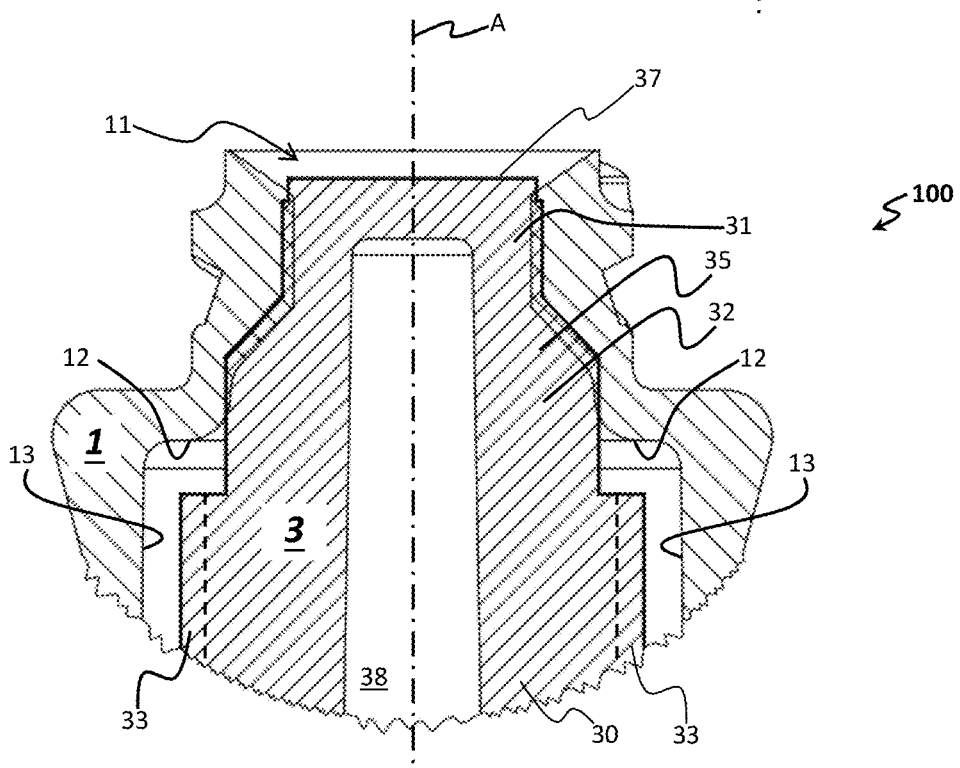
FIG. 1c is a close-up view based on detail K from FIG. 1b.

FIG. 1a is side view of an exemplary assembly according to the present disclosure. FIG. 1b is H-H section of the assembly based on FIG. 1a. FIG. 1c is a close-up view based on detail K from FIG. 1b. Referring to FIG. 1a to FIG. 1c, the assembly (100) comprises an attachment part (1) for removably engaging a delivery device. The assembly (100) further comprises a connection part (2) for connecting to a container. Considering the terminology used in the related art, the attachment part (1) can be also named as a "cap" or "upper part of the valve", and the connection part (2) as a "lower part of the valve".

Figure 2A:
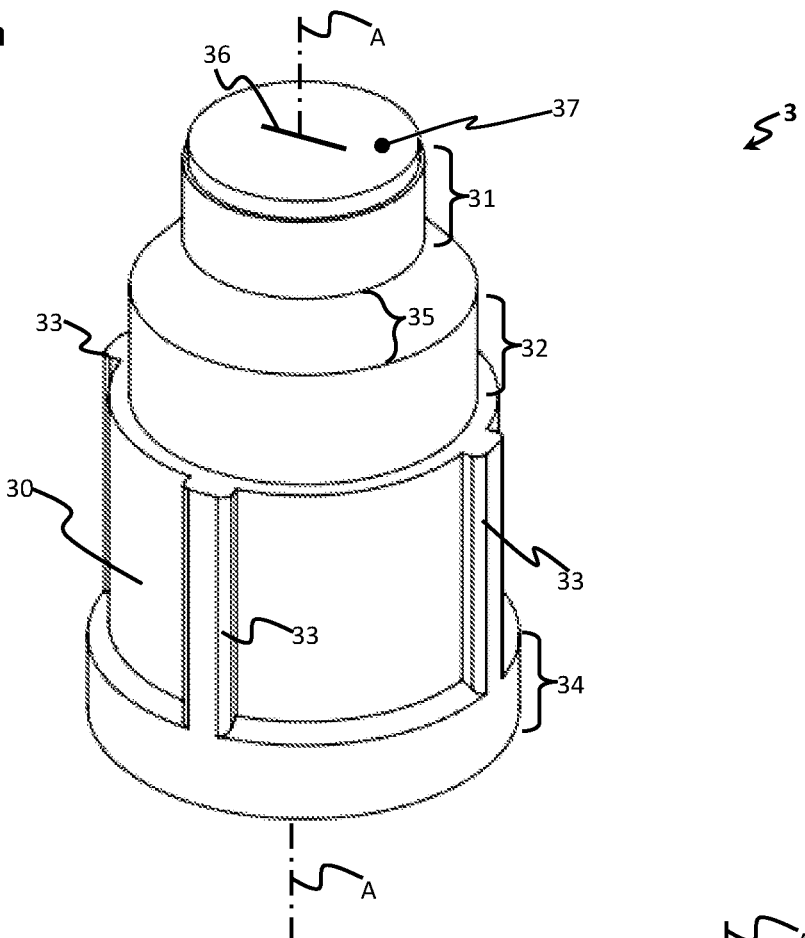
FIG. 2a is perspective view of an exemplary sealing member embodiment for an assembly according to the present disclosure.
Figure 2B:
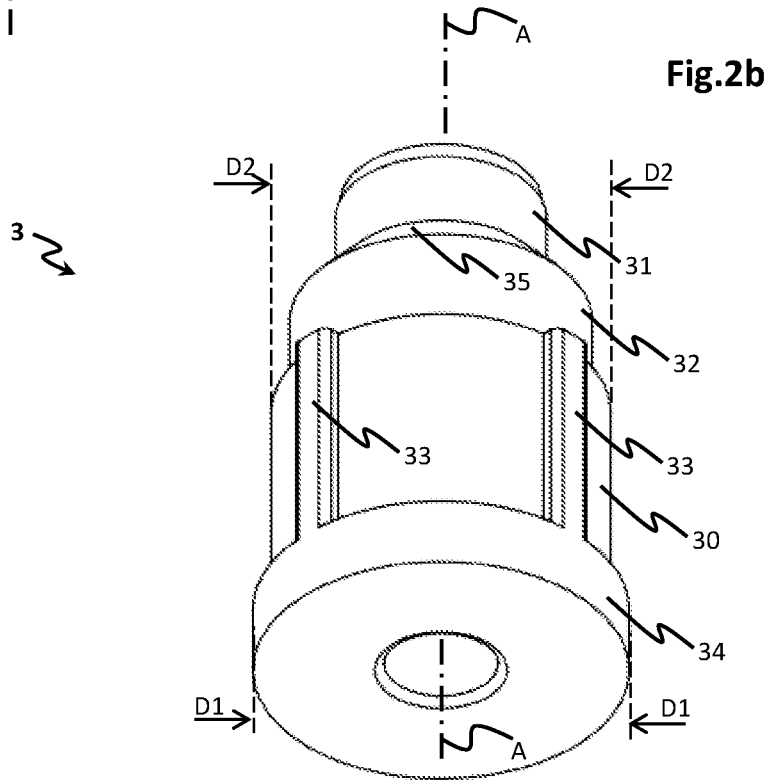
Figure 4A:
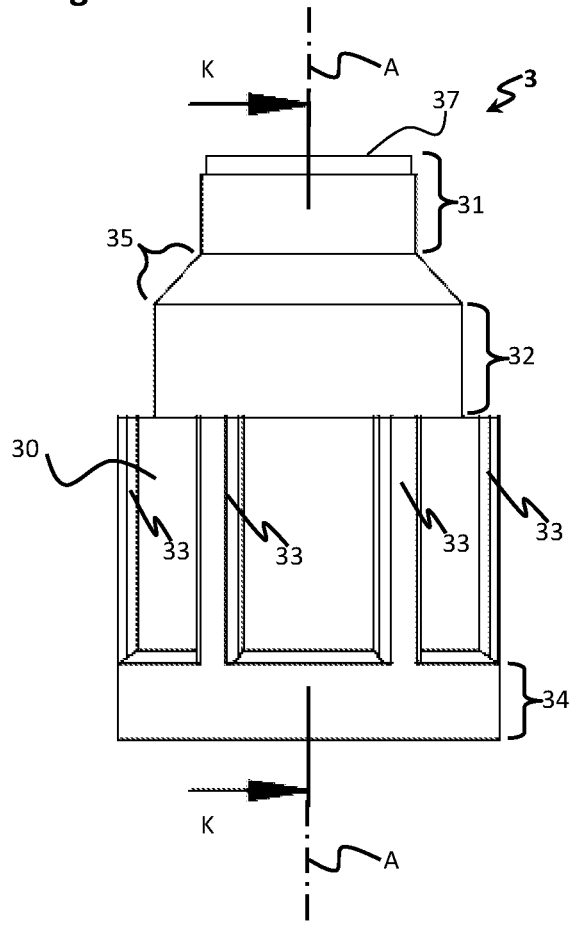
FIG. 4a is side view of another exemplary embodiment of the sealing member according to the present disclosure.
Figure 4B:
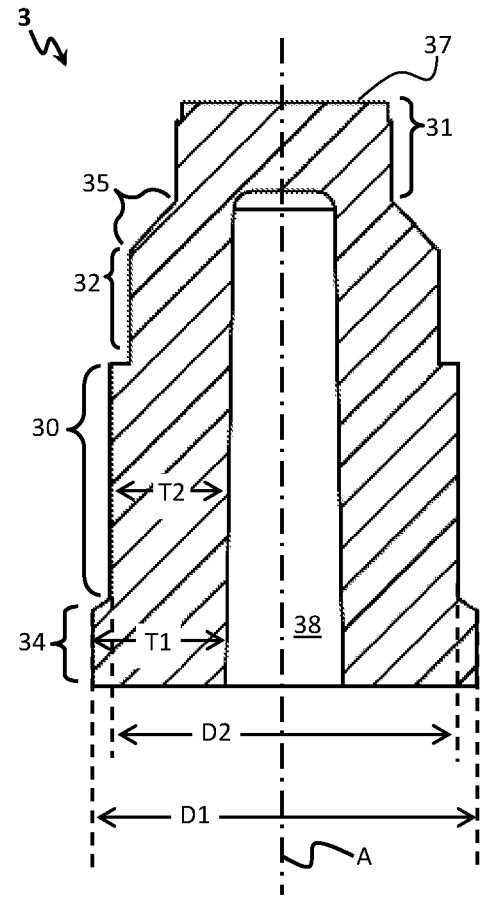
Figure 4C:
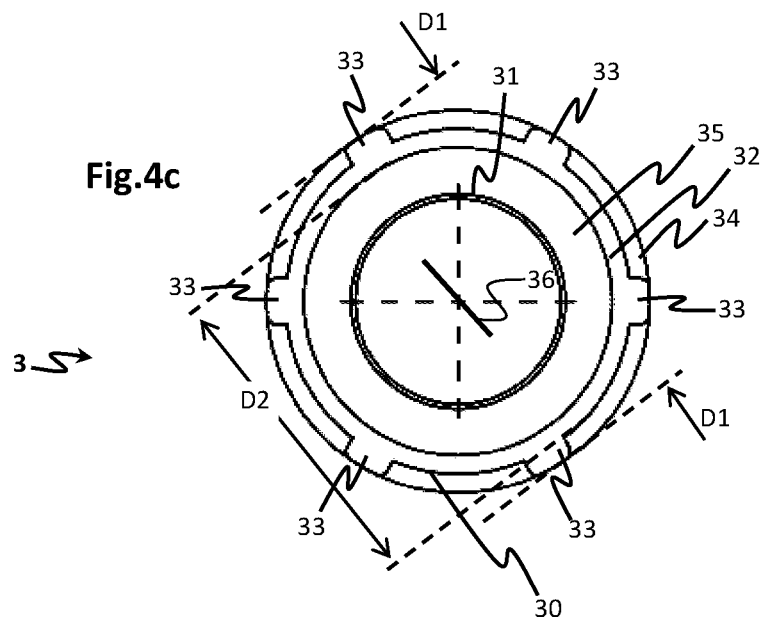

The assembly (100) further comprises a flexible sealing member (3) circumferentially enclosed between the attachment part (1) and connection part (2) around a main axis (A). FIG. 2a is perspective view of an exemplary sealing member embodiment for an assembly according to the present disclosure. FIG. 2b is another perspective view of the sealing member shown in FIG. 2a. FIG. 3a is side view of an exemplary embodiment of the sealing member according to the present disclosure. FIG. 3b is J-J section view of the sealing member based on FIG. 3a. FIG. 3c is plan view of the sealing member shown in FIG. 3a. FIG. 4a is side view of another exemplary embodiment of the sealing member according to the present disclosure. FIG. 4b is K-K section view of the sealing member based on FIG. 4a. FIG. 4c is plan view of the sealing member shown in FIG. 4a. FIG. 5a shows perspective view of another exemplary embodiment of the sealing member according to the present disclosure. FIG. 5b is plan view of the sealing member shown in FIG. 5a. FIG. 5c is another perspective view of the sealing member shown in FIG. 5a.

Referring to FIG. 2a to FIG. 5b; the sealing member (3) comprises a cylindrical body (30) extending along the axis (A). The sealing member (3) further comprises a sealing head (31) at an axially distal end of the sealing member (3) with regard to the body (30). The sealing head (31) can be considered arranged for being partially exposed through an access opening (11) of the attachment part (1). The sealing member (3) further comprises a cylindrical portion (32) between the body (30) and head (31).

Figure 6A:
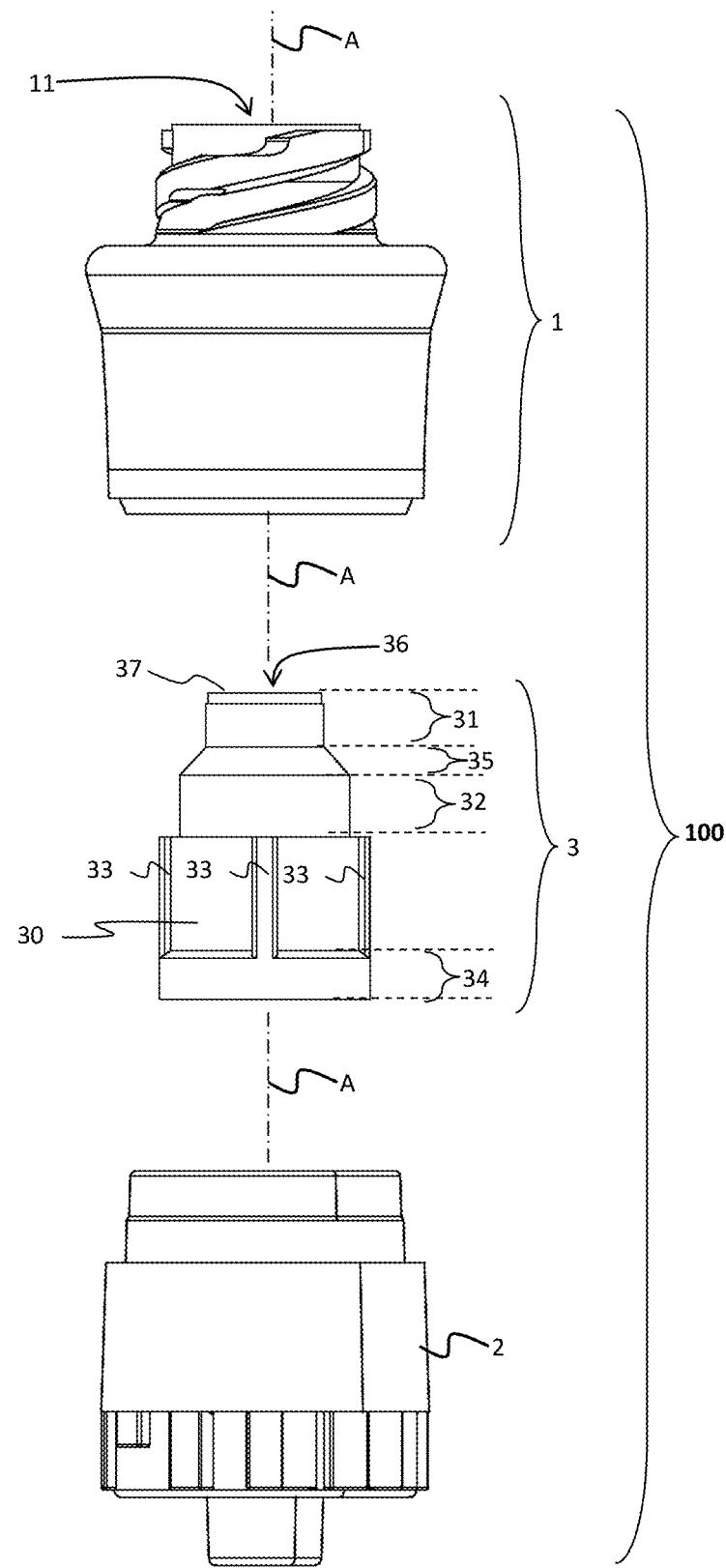
FIG. 6a is exploded side view of an exemplary assembly according to the present disclosure.
Figure 6B:
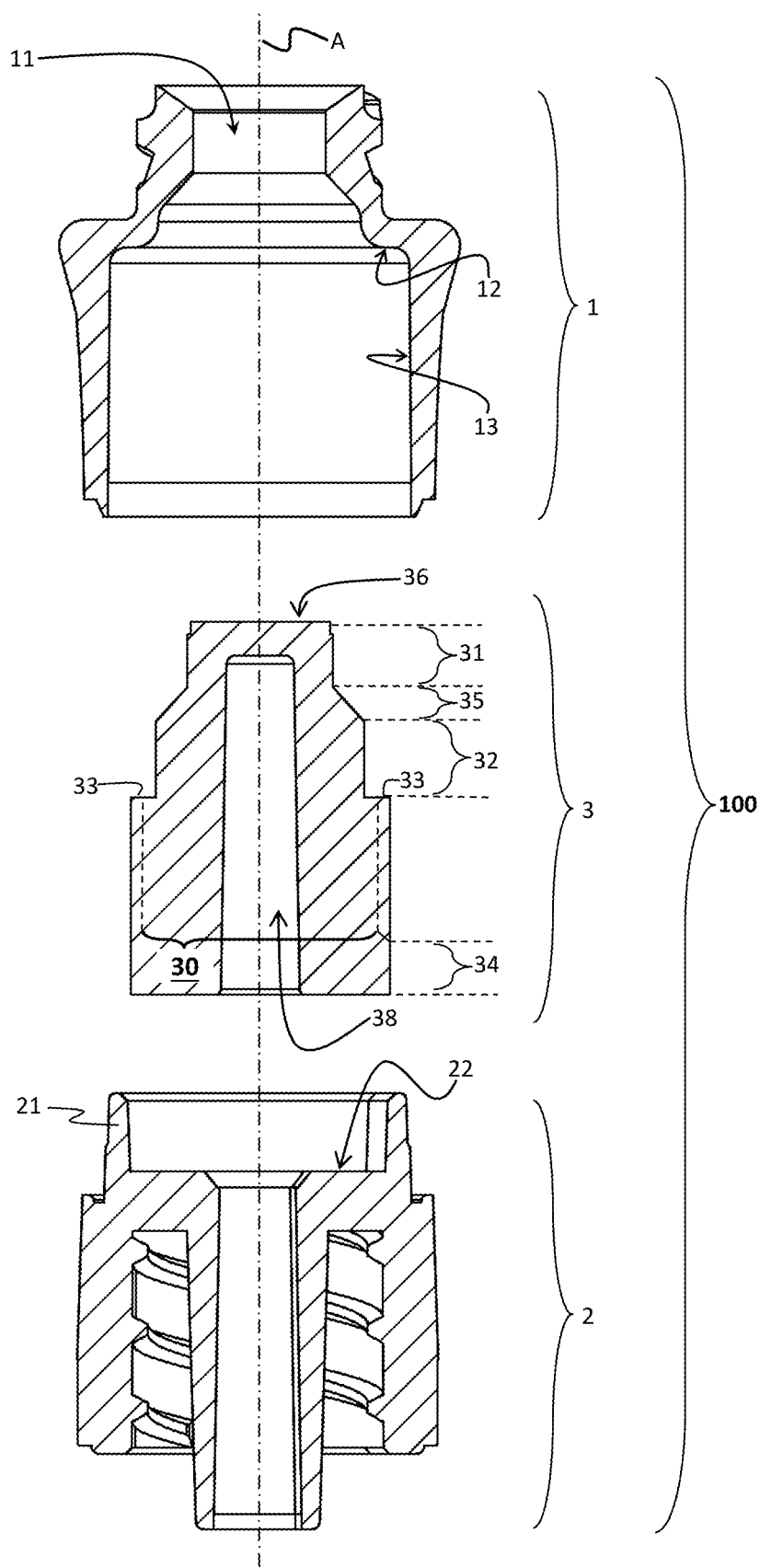

FIG. 6a is exploded side view of an exemplary assembly according to the present disclosure. FIG. 6b is exploded section view of the assembly shown in FIG. 6a. Referring to FIG. 6a and FIG. 6b, it can be considered that:
 the attachment part (1) has a hollow structure for axially receiving the sealing member (3) through an opening at a first side of the attachment part (1) that is arranged for engagement with the connection part (2), such that the head (31) is exposed through an access opening (11) that is distal to said first side;

the sealing member (3) is axially held between the attachment part (1) and connection part (2) when the attachment part (1) and connection part (2) are attached to one another;

when the attachment part (1) and connecting part (2) attached to one another, a foot portion (34) of the sealing member (3) distal to the head (31) rests with a lower side thereof on a seating surface (22) of the connection part (2);

the attachment between the attachment part (1) and the connecting part (2) can be arranged by first introducing the sealing member (3) into the attachment part (1) such that the head (31) opposes or partially enters into the access opening (11), then engaging the connecting part (2) to a distal end of the attachment part (1) with regard to the access opening (11);

alternatively, said attachment can be performed by placing the foot portion (34) of the sealing member (3) onto the attachment part (1), for instance between one or more side walls (21) arranged for holding the foot portion (34) against radial movements with regard to the axis (A); then engaging the attachment part (1) onto the connecting part (2), such that the sealing member (3) is introduced into the connecting part (2) and the head (31) opposes and then at least partially enters into the access opening (11).

Accordingly, one or more of the following can be taken into consideration:

the sealing member (3) can comprise a foot portion (34) at an axially distal end of the sealing member (3) with regard to the head (31); the foot portion (34) can be arranged for being in mechanical communication with the connection part (2).

the connection part (2) can comprise a side wall (21) that is sized and shaped for supporting the foot portion (34) in radial directions towards the axis (A); thus, said mechanical communication between the foot portion (34) and the connection part (2) is available at an enhanced extent in both of the first and second states.

The sealing member (3) is arranged to have a closed first state in which the head (31) is received into an access opening (11) of the attachment part. The sealing member (3) is further arranged to have an open second state in which the head (31) is retracted away from the access opening (11) (that is, towards the connection part 2) when compressed through the access opening (11) along the axis (A). For visualization of the open second state, FIG. 7a gives a side view of the exemplary assembly shown in FIG. 1, in engagement with a delivery device. FIG. 7b is side section view based on FIG. 7a. FIG. 8a is perspective section view based on FIG. 7b. FIG. 8b is close-up view of detail M from FIG. 8a.

It can be considered that the attachment part (1) comprises a first inner wall surface (12) that extends transverse or orthogonal with respect to the axis (A), and opposes the connection part (2) in the direction of axis (A). Throughout the present specification, the first inner wall surface (12) can also be referred to as axially opposing inner surface (12).

It can be further considered that the attachment part (1) comprises a second inner wall surface (13) that opposes the sealing member (3) (e.g., the body 30) radially with respect to the axis (A), such that a circumferential gap remains in-between the sealing member (3) and the second inner wall surface (13) at least when in the first position. Throughout the present specification, the first inner wall surface (13) can also be referred to as second inner wall surface (13).

Body (30) of the sealing member (3) is shaped and sized for maintaining a non-contact mechanical status with regard to the first inner wall surface (12).

For instance, the body (30) can be shaped and sized for maintaining a positive value of distance to respective one or more first inner wall surfaces (12) of the attachment part (1), when in the first state. Therefore, sealing member (3) does not contact to such first inner wall surfaces (12). So, when the sealing member (3) is axially compressed at the head (31) at taking the second state, radial widening of the body (30) is not obstructed by radially oriented friction forces between the sealing member (3) and respective first inner wall surfaces (12). This enables the transition from the closed first state to the open second state to take place with a decreased extent of effort by an operator that introduces a tip (80) of a delivery device. Thus, the above-mentioned positive value of distance provides ease of use to the assembly (100).

Referring again to FIG. 2a to FIG. 5c, the sealing member (3) can comprise one or more columns (33) on a side surface of the body (30). The columns (33) radially protrude away from the axis (A), and extend parallel to the axis (A) along the body (30). The columns (33) provide an increased extent of resilience and potential energy accumulating capacity to the sealing member (3), in particular, to the body (30). This results in a facilitated recovery of the first state upon cessation of the axial compression onto the head (31). As a result, the transition from the closed first state to the open second state, as well as the transition to the closed first state from the open second state, are facilitated.

In such embodiment, the one or more columns (33) are sized and shaped for maintaining said positive value of distance to respective one or more first inner wall surfaces (12) of the attachment part (1), when in the first state. Therefore, the columns (33) do not contact to such first inner wall surfaces (12). So, when the sealing member (3) is axially compressed at the head (31) at taking the second state, radial widening of the body (30) is not obstructed by radially oriented friction forces between the columns (33) and respective first inner wall surfaces (12). This enables the transition from the closed first state to the open second state to take place with a decreased extent of effort by an operator that introduces a tip (80) of a delivery device. Thus, the above-mentioned positive value of distance provides ease of use to the assembly (100).

In a possible embodiment, the body (30) can be sized and shaped for maintaining a positive value of distance to a second inner wall surface (13) of the attachment part (1), when in the normally closed first state. In the case where the body (30) is provided with columns (33), the columns (33) can be sized and shaped for maintaining a positive value of distance to a second inner wall surface (13) of the attachment part (1), at least when in the normally closed first state. So, in such embodiments, the body (30) (that may be provided with columns (33)) is arranged with radial play with respect to respective inner side surfaces (that is, second inner wall surfaces 13) of the attachment part (1). Thus, the sealing member (3) is easily deformed in radial directions with regard to the axis (A) when forced to the second state.

In a preferred embodiment, the sealing member (3) comprises three or more columns (33), which can be equally distributed around the axis (A). That is, in the case of three columns, radial angles in-between adjacent columns are 120 degrees each, on the basis of 360 degrees of full angle around the axis (A). Likewise, in the possible cases of four, six or eight columns, radial angles in-between adjacent columns can be 90, 60 or 45 degrees, respectively. This provides an enhanced extent of geometric uniformity to the sealing member (3) around the axis (A), at transition from the closed first state to the open second state. The sealing member (3) can comprise four or more columns (33), for example, six columns (33) that are equally distributed around the axis (A). As exemplary visualizations thereto, each of the sealing members (3) depicted in FIG. 2a to FIG. 3c and in FIG. 5a to FIG. 5c comprise four columns (33) that are equally distributed around respective axes (A) with 90 degrees of radial angles in-between columns that are adjacent to one another; whereas the sealing member (3) depicted in FIG. 4a to FIG. 4c comprise six columns (33) that are equally distributed around respective axes (A) with 60 degrees of radial angles in-between columns that are adjacent to one another, on the basis of 360 degrees full angle.

The sealing member (3) can comprise a slot opening (36) for receiving a tip (80) of a needle-free delivery device at being brought to the second state. FIG. 2a, FIG. 3c, FIG. 4c and FIG. 5b schematically show exemplary positioning and shape of a slot opening (36) formed on a head (31).

The foot portion (34) can axially extend from the body (30) away from the head (31). Referring to FIG. 6b in conjunction with FIG. 1b and FIG. 7b, the foot portion (34) can be considered arranged to be in an annular contact with a respective seating surface (22) of the connection part (2) around the axis (A), thereby providing a sealing in radial directions with regard to the axis (A).

With reference to FIG. 3b and FIG. 4b, in radial directions with regard to the axis (A), the foot portion (34) can have a greater thickness (T1) when compared to a thickness (T2) of the body (30). In this embodiment, the sealing member (3) inherently has an increased resilience at the foot portion (34) due to the increased material thickness at the same. As a result, the foot portion (34) substantially or fully retains its geometric shape even at transitions of the sealing member (3) between the open and closed states. Considering that the connection part (2) is inherently in contact with a corresponding surface of the foot portion (34) around the axis (A), and that the connection part (2) is inherently built of a rigid (that is, substantially less flexible) material when compared to the building material of the sealing means (3); this feature provides an enhanced extent of sealing between the foot portion (34) and connection part (2) in radial directions with regard to the axis (A). For instance, an inner diameter of the sealing member (3) at the body (30) and foot portion (34) can be substantially the same (e.g., with a difference within the range between 0 and 10 percent); and the foot portion (34) can have an outer diameter (D1) that is greater than an outer diameter (D2) of the body (30) (e.g., with a difference that is greater than 10 percent, for example, 20 percent or greater). In other words, a ratio of the thickness (T1) at the foot portion (34) to the thickness (T2) at the body (30) is 1.1:1.0 or greater, for example, 1.2:1.0 or greater.

FIG. 2b, FIG. 3c and FIG. 4c schematically visualizes exemplary comparisons between the diameter (D1) of the foot portion (34) and diameter (D2) of respective body (30) in different exemplary embodiments of the sealing means (3). A similar comparison can be also made by observing the FIG. 5b which shows plan view of another exemplary embodiment of sealing means (3) within the context of the present disclosure.

In a possible embodiment, the difference between a radius of the foot portion (34) and a radius of the body (30) is equal to a radial protrusion extent of the one or more columns (33). In other words, a half of the difference between the diameter (D1) of the foot portion (34) and the diameter (D2) of the body (30) is equal to a radial protrusion extent of the one or more columns (33). Thus, axial projections of the columns (33) towards the connection part (2) substantially or fully coincide with the foot portion (34). This measure reduces the geometric complexity and facilitates formation of the sealing member by molding. FIG. 1b and FIG. 2a to FIG. 6b show various exemplary sealing members (3) in accordance with this measure. The sealing member (3) can be made from a silicon-based elastomeric material as commonly employed in the related art.

The side wall (21) can be sized and shaped to circumferentially cover the foot portion (34) around the axis (A). So, when placed onto the connection part (2) at assembling, the sealing member (3) is held in place and easily introduced into the attachment part (1) at engaging the connection part (2) thereto. Furthermore, when in use, obstruction of medical fluid leakage between striking surfaces of the connection part (2) and sealing member (3) is available not only in radial directions, but also in directions that are parallel to the axis (A). Examples of assemblies (100) according to this embodiment are particularly depicted in FIG. 1b, FIG. 6b, FIG. 7b and FIG. 8b.

In a possible embodiment, the sealing member (3) comprises a cylindrical portion (32) between the body (30) and head (31). Diameter of the cylindrical portion (32) can be smaller than the diameter (D2) of the body (30), and greater than that of the head (31). The sealing member (3) comprises an intermediate portion (35) between the body (30) and head (31). It can be considered that the intermediate portion (35) is disposed between the cylindrical portion (32) and head (31). The intermediate portion (35) can have a frusto-conical geometry, diameter of which decreases from the cylindrical portion (32) towards the head (31). With reference to FIG. 1b and FIG. 1c, the intermediate portion (35) can be considered arranged for being in mechanical contact with a corresponding inner surface of the attachment part (1) when in the closed first state; such that the sealing member (3) is clamped in-between the attachment part (1) and connection part (2) at the intermediate portion (35) and foot portion (34), respectively. The intermediate portion (35) having a geometry of frustum of a cone minimizes friction force components parallel to the axis (A) between the sealing member (3) and attachment part (1) at transitions between the closed first state and open second state. This fact further facilitates the transition from the closed first state to the open second state.

The attachment part (1) and/or connection part (2) can include a Luer fitting such as Luer slip or Luer lock connector, for example, Luer lock connector for creating a threaded connection with the delivery device or container of further medium, respectively. The access opening (11) of the attachment part (1) can be formed on a female fitting, such as female Luer slip fitting or, female Luer lock fitting. The connection part (2) can include a male Luer fitting, such as a male Luer lock fitting that provides hydraulic communication to the sealing member-side of the head (34) through an inner cavity (38) of the sealing member (3). When the open second state takes place, a flow path is established between the access opening (11) and the fitting on the connection part (2). In the examples visualized in FIG. 1a, FIG. 1b, FIG. 6a and FIG. 6b, respective access openings (11) of the exemplary attachment parts (1) are formed on female Luer lock fittings, and connection parts (2) include respective male Luer lock fittings.

The way of functioning of the assembly (100) according to the present disclosure can be also formulated as follows:

The assembly (100) can be considered as a swabbable needle free valve having a collapsible sealing member (3), outer side walls of which is reinforced with the one or more columns (33). The sealing member (3) can be considered as an elastomeric valve stem. The attachment part (1) and connection part (2) constitute a valve body, or housing, when attached to one another.

Connection part (2) of the assembly (100) as a swabbable needle-free valve can be connected to an intravenous (IV) line, a container, and the like. In the closed first state, the head (31) is pushed shut inside the access opening (11) to prevent fluid flow therethrough. When accessed by a tip (80) of a delivery device, such as a male Luer slip or Luer lock fitting tip on the end of a syringe or another IV component, the tip (80) forces the valve stem inwardly into the valve body upon which the tip (80) enters the slot opening (36) to open the valve stem and permit fluid flow to or from the delivery device, through its tip (80), and also through the now forced-open slot opening (36). Thus, the open second state takes place. FIG. 7a to FIG. 8b schematically visualize engagement with a tip (80) of a delivery device that result in transition from the closed first state to the open second state. Thanks to the geometric considerations of the one or more columns (33) and the elastomeric qualities of the sealing member (3), the sealing member (3) resiliently expands towards the access opening (11) to return to its normally-closed first state, once the tip (80) of the delivery device is removed from the assembly (100).

Once the tip (80) of the access device is removed from the assembly (100), columns (33) of the collapsible sealing member (3) assist the head (31) to enter into and be radially supported by the access opening (11). This easily results in closure of the slot opening (36) and thus, of the flow path. As a result, any leakage of medical fluid through the slot opening (36) or access opening (11) is prevented. With arrangement of size and shape of the attachment part (1) and sealing member (3) or head (31), a proper closure can be considered to correspond to an automatic axial level alignment between a top exposed surface (37) of the head (31) and an upper surface of the attachment part (1). Within this context, the exposed surface (37) of the head (31) can be flat, that is, planar. This facilitates wetting of the head (31), in other words, spreadability of a disinfecting solution of a cleaning cap for an effective swabbing.

Figure 9A:
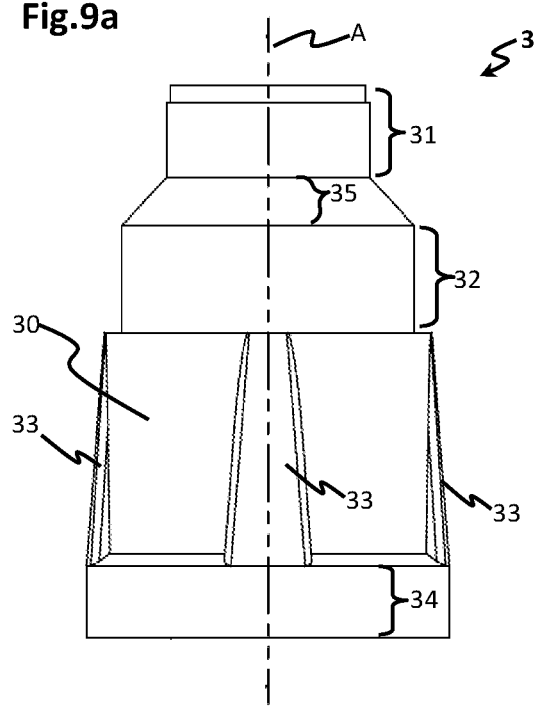
FIG. 9a is side view of an exemplary sealing member embodiment for an assembly according to the present disclosure.
Figure 9B:
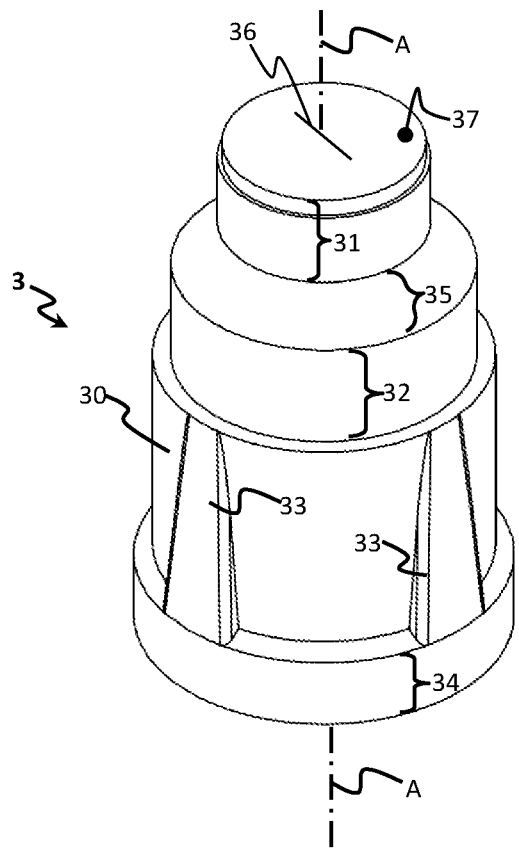
Figure 9C:
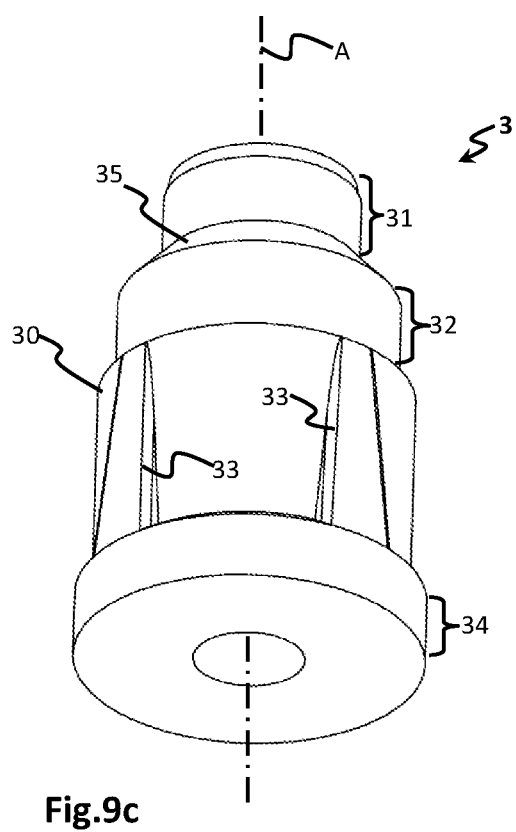

FIG. 9a shows side view of a collapsible sealing member (3) in a further possible embodiment according to the present disclosure, columns (33) of which are further distanced from the second inner wall surface (13) of the attachment part (1) at regions that are relatively proximal to the access opening (11) with regard to the foot portion (34). FIG. 9b and FIG. 9c respectively show upper and lower perspective views of the collapsible sealing member (3) from FIG. 9a. With reference to FIG. 9a to FIG. 9c, the one or more columns (33) of the collapsible sealing member (3) can have a tapered geometry, radial width of which decreases from the foot portion (34) towards the cylindrical portion (32). This measure further increases the radial distance between the columns (33) from the second inner wall surface (13).

FIG. 10a shows side view of a collapsible sealing member (3) in a further possible embodiment according to the present disclosure, which is not provided with columns (33); yet the body (30) of which is further distanced from the first inner wall surface (13) of the attachment part (1), e.g., over the size and shape of the cylindrical portion (32) to axially extend relatively more towards the foot portion (34), thereby resulting in a axially shorter body (30) when compared to the embodiments with columns (33). FIG. 10b and FIG. 10c respectively show upper and lower perspective views of the collapsible sealing member (3) from FIG. 10a. With reference to FIG. 10a to FIG. 10c, the one or more columns (33) of the collapsible sealing member (3) can have a stepped geometry, radial width of which decreases from the foot portion (34) towards the cylindrical portion (32). This measure also increases the radial distance between the sealing member (3) from the second inner wall surface (13). In accordance with this measure, the sealing member (3) can be arranged to maintain a positive value of radial distance from the second inner wall surface (13) even at the instances where it is axially compressed to take the open second state. Thus, it is rendered possible that the side surfaces of the body (30) of the sealing member (3) does not touch to the inner walls when radially spread under axial pressure that can be exerted by a male luer tip through the access opening (11). In such embodiment, in order to provide an enhanced extent of resilience to the sealing member (3) with regard to the embodiments with columns (33); the foot portion (34) can have an increased axial length that axially extends out from the side wall (21) of the attachment part (1) towards the access opening (11).

REFERENCE SIGNS 1 attachment part
11 access opening
12 first inner wall surface (of the attachment part)
13 second inner wall surface (of the attachment part)
2 connection part
21 side wall (of the attachment part)
22 seating surface
3 sealing member
30 body
31 head
32 cylindrical portion
33 column
34 foot portion
35 intermediate portion
36 slot opening
37 exposed surface
38 inner cavity (of the sealing member)
80 tip
100 assembly
A axis
D1 diameter of the foot portion
D2 diameter of the body
T1 thickness of the foot
T2 thickness of the body

The invention claimed is:

1. A connector assembly for communication of medical liquids, comprising an attachment part for removably engaging a delivery device, a connection part for connecting a container, and a flexible sealing member circumferentially enclosed between the attachment part and connection part around a main axis (A);

the attachment part comprises a first inner wall surface that extends orthogonal with respect to the axis (A), and opposes the connection part in the direction of axis (A);
the sealing member comprises a cylindrical body extending along the axis (A) and having an outer surface having a diameter (D2), a sealing head at an axially distal end of the sealing member with regard to the cylindrical body, the sealing member arranged to have a closed first state in which the head is received into an access opening of the attachment part, and an open second state in which the head is retracted away from the access opening when compressed through the access opening along the axis (A);

the sealing member having a foot portion at an axially distal end of the sealing member with regard to the head, arranged for being in mechanical contact with the connection part, the foot portion having a diameter (D1) greater than the diameter of the cylindrical body;

wherein the cylindrical body is shaped and sized for maintaining a non-contact mechanical status with regard to the first inner wall surface;

the sealing member further comprises columns on a side surface of the cylindrical body;

the columns radially protruding away from the axis (A), and extending parallel to the axis (A) along the cylindrical body;

the columns are sized and shaped for, when in the first state, maintaining a positive value of distance to the respective first inner wall surface of the attachment part;

a diameter of the sealing member around the axis (A) does not decrease in-between the cylindrical body and the foot portion; and each of the columns includes an outer surface, a first end, and a second end, wherein the first end of each of the columns is distal to the foot portion and the second end of each of the columns terminates at the foot portion, the outer surface of each of the columns is spaced from the axis (A) a distance equal to the distance that the outer surface of the foot portion is spaced from the axis (A).

2. The connector assembly according to claim 1, wherein the attachment part comprises a second inner wall surface that opposes the sealing member radially with respect to the axis (A), such that a circumferential gap remains in-between the sealing member and the second inner wall surface at least when in the first position; and the cylindrical body is sized and shaped for maintaining a positive value of distance to the second inner wall surface of the attachment part, when in the normally closed first state.

3. The connector assembly according to claim 1, wherein the columns are sized and shaped for, when in the first state, maintaining a positive value of distance to a second inner wall surface of the attachment part.

4. The connector assembly according to claim 1, wherein the columns of the collapsible sealing member have a tapered geometry, such that a radial width of the one or more columns decreases from the foot portion towards the cylindrical portion.

5. The connector assembly according to claim 1, wherein in radial directions with regard to the axis (A), the foot portion has a greater thickness (T1) when compared to a thickness (T2) of the cylindrical body.

6. The connector assembly according to claim 5, wherein an inner diameter of the sealing member at the cylindrical body and foot portion has an identical value or has a difference of up to 10 percent; and the foot portion has an outer diameter (D1) that is greater than an outer diameter (D2) of the cylindrical body by an amount that is greater than 10 percent.

7. The connector assembly according to claim 6, wherein the outer diameter (D1) of the foot portion is greater than an outer diameter (D2) of the cylindrical body by an amount that is greater than 20 percent.

8. The connector assembly according to claim 1, wherein the foot portion axially extends from the cylindrical body and has a diameter (D1) that is greater than a diameter (D2) of the cylindrical body.

9. The connector assembly according to claim 1, wherein the connection part comprises a side wall that is sized and shaped for supporting the foot portion in radial directions towards the axis (A).

10. The connector assembly according to claim 9, wherein the side wall is sized and shaped to circumferentially cover the foot portion around the axis (A).

11. The connector assembly according to claim 1, wherein the sealing member comprises a cylindrical portion between the cylindrical body and head.

12. The connector assembly according to claim 1, wherein the sealing member comprises an intermediate portion between the cylindrical body and head, the intermediate portion having a frusto-conical geometry with a diameter that decreases towards the head.

13. The connector assembly according to claim 12, wherein the sealing member comprises a cylindrical portion between the cylindrical body and head, and the intermediate portion is disposed between the cylindrical portion and head.

14. The connector assembly according to claim 1, wherein the sealing member comprises a slot opening for receiving a tip of a delivery device when in the second state.

15. The connector assembly according to claim 1, wherein the attachment part comprises a female Luer lock fitting on which the access opening is formed, and the connection part includes a male Luer lock fitting in hydraulic communication with an inner cavity of the sealing member.

16. A connector assembly for medical liquids comprising:
an attachment part configured to engage a delivery device, the attachment part defining an access opening and including a first inner wall surface and a second inner wall surface;
a connection part coupled to the attachment part to define a main axis, the connection part having a seating surface, the first inner wall surface extending orthogonal to the main axis and being opposed to the connection part; and
a flexible sealing member received between the attachment part and the connection part and including a sealing head, a cylindrical body having an outer surface that defines a first diameter, and a foot portion having an outer surface that defines a second diameter that is greater than the first diameter, the sealing head supported on a first end of the cylindrical body and the foot portion supported on a second end of the cylindrical body, the foot portion engaged with the seating surface of the connection part, the sealing head received within the access opening of the attachment part, the flexible sealing member having columns that extend along the outer surface of the cylindrical body and have an outer surface that is spaced from the main axis a distance equal to the distance that the outer surface of the foot portion is spaced from the main axis adjacent the foot portion.

17. The connector assembly according to claim 16, wherein the cylindrical body of the flexible sealing member is spaced from the second inner wall surface of the attachment part.

18. The connector assembly according to claim 16, wherein the columns extend from the foot portion along the cylindrical portion towards the sealing head.

19. The connector assembly according to claim 16, wherein the flexible sealing member includes three or more columns equally spaced about the main axis.

20. The connector assembly according to claim 16, wherein the flexible sealing member includes four columns.

* * * * *